United States Patent [19]
Haslwanter et al.

[11] Patent Number: 5,897,858
[45] Date of Patent: Apr. 27, 1999

[54] NASAL SPRAY COMPOSITIONS EXHIBITING INCREASED RETENTION IN THE NASAL CAVITY

[75] Inventors: Joseph A. Haslwanter, Germantown; William F. Rencher, Cordova, both of Tenn.

[73] Assignee: Schering-Plough Healthcare Products, Inc., Memphis, Tenn.

[21] Appl. No.: 08/964,038

[22] Filed: Nov. 4, 1997

Related U.S. Application Data

[63] Continuation of application No. 08/375,014, Jan. 19, 1995, abandoned, which is a continuation-in-part of application No. 08/191,402, Feb. 3, 1994, abandoned.

[51] Int. Cl.$^6$ ...................................................... A61K 9/08
[52] U.S. Cl. .................... 424/78.04; 424/78.08; 424/601; 424/434; 424/78.04; 514/912; 514/853; 514/772.5; 514/937
[58] Field of Search .................. 424/45, 195.1, 424/78.08, 601, 434, 78.04; 514/772.5, 937, 912, 853

[56] References Cited

U.S. PATENT DOCUMENTS

| | | | |
|---|---|---|---|
| 4,581,225 | 4/1986 | Su et al. ...................................... | 424/45 |
| 5,114,979 | 5/1992 | Kielley ...................................... | 514/783 |
| 5,116,847 | 5/1992 | Gilbert et al. ........................... | 514/853 |

FOREIGN PATENT DOCUMENTS

| | | |
|---|---|---|
| 109561 | 5/1984 | European Pat. Off. . |
| 0 380 367 | 8/1990 | European Pat. Off. . |
| 0454617 | 10/1991 | European Pat. Off. . |
| 0571671 | 12/1993 | European Pat. Off. . |
| 94/05330 | 3/1994 | WIPO . |

OTHER PUBLICATIONS

Gennaro, A. R. (1985). Remington's Pharmaceutical Sciences, Mack Pub., Co., pp. 889 & 1500.
Martindale—The Extra Pharmacopoeia (1989) p.841.
Remington's Pharmaceutical Sciences (1985) pp. 889, 1127, 1159, 1299, 1305, 1309 and 1500, Mack Publishing Co.
Chem Abs. vol. 116; No. 18; No. 181179, May 7, 1992, JP–A–04026617.
Chem Abs vol. 108; No. 24, No. 210213, Jun. 13, 1988, JP–A–62223131.

*Primary Examiner*—Raj Bawa
*Attorney, Agent, or Firm*—Arthur Mann; John J. Maitner

[57] ABSTRACT

Aqueous nasal spray compositions containing:

0.001–2% by weight/volume of a medicament selected from the group consisting of chlorpheniramine maleate, oxymetazoline hydrochloride and mixtures thereof;

0.50 to 15.00% by weight/volume of a water soluble polymer selected from the group consisting of polyvinylpyrrolidone having an average molecular weight of about 10,000 to 360,000 and mixtures thereof;

2.5 to 10.00% by weight/volume of polyethylene glycol;

1.00 to 10.00% by weight/volume of a moisturizing agent other than polyethylene glycol;

0.01 to 0.05% by weight/volume of disodium edetate;

0.001 to 0.3% by weight/volume of an antimicrobial preservative;

0.20 to 5.00% by weight/volume of an aromatic alcohol;

a sufficient amount of a pharmaceutically acceptable buffer to maintain the pH of the composition within the range of about 4.0 to 8.0; and QS water.

11 Claims, No Drawings

NASAL SPRAY COMPOSITIONS EXHIBITING INCREASED RETENTION IN THE NASAL CAVITY

This is a continuation of application Ser. No. 08/375,014 filed Jan. 19, 1995; now abandoned which was a continuation-in-part of Ser. No. 08/191,402 filed Feb. 3, 1994, now abandoned.

BACKGROUND OF THE INVENTION

This invention relates to aqueous nasal compositions comprising a medicament in an aqueous carrier containing a water soluble polymer selected from the group of polyvinylpyrrolidone and mixtures thereof. The combination of water soluble polymers provides unexpected properties which enhance medicinal efficacy and promotes organoleptic acceptance of the compositions One of the major hindrances to effective systemic absorption of medicaments such as chlorpheniramine maleate in the nose is due to anatomical features of the epithelium within the nasal cavity. The constant beating of the nasal cilia causes the mucus film to continually move toward the nasopharynx. This action, in about 8 to 10 minutes, will remove the medicament from the nasal mucosa reducing the time for effective systemic absorption.

Certain medicaments are active topically and are not systemically absorbed, such as the topically active nasal decongestant oxymetazoline hydrochloride. This medicament is a vasoconstrictor that increases nasal airway volume by reducing blood flow to the nasal capillary bed. Oxymetazoline hydrochloride also reduces blood flow to the muco-secreting cells and as a result reduces nasal secretions. This reduction of natural moisture replacement in conjunction with moisture vaporization due to increased air flow volume promotes drying of the nasal cavity. Loss of this protective mucosal film may result in an increased occurrence in nasal sensitivity and associated burning and stinging.

It is known that when a combination of medicaments, such as chlorpheniramine maleate and oxymetazoline hydrochloride are incorporated into typical nasal spray formulations the occurrence of nasal burning and stinging increases.

Nasal drying and the associated stinging within the nasal cavity is one of the most common complaints of patients and consumers that use nasal spray products. Other common nasal product negative attributes include odor, taste and the tendency of the product to run out of the nose.

We have surprisingly discovered that incorporation of a combination of water soluble polymers selected from the group consisting of polyvinylpyrrolidone, polyethylene glycol and mixtures thereof into nasal spray compositions provide enhanced medicinal efficacy and promotes organoleptic acceptence of the compositions.

It is an object of the present invention to provide nasal spray compositions exhibiting increased nasal retention of medicaments in the nasal cavity for enhanced topical or systemic activity.

Another object of the present invention is to provide nasal spray compositions exhibiting reduced post nasal drip.

It is a further object of the present invention to provide nasal spray compositions exhibiting increased moisturization in the nasal cavity.

A further object of the present invention is to provide nasal spray compositions which reduce the potential of medicament induced stinging, burning, overdrying or irritation.

SUMMARY OF THE INVENTION

The present invention provides aqueous nasal spray compositions comprising a medicament and an aqueous carrier containing a water soluble polymer selected from the group consisting of polyvinylpyrrolidone and mixtures thereof.

The present invention provides aqueous nasal spray compositions comprising an effective amount of a medicament in an aqueous carrier comprising:

0.50 to 15.00% by weight/volume of a water soluble polymer selected from the group consisting of polyvinylpyrrolidone and mixtures thereof;

0.00 to 15.00% by weight/volume of polyethylene glycol;

0.00 to 10.00% by weight/volume of a moisturizing agent or mixtures of moisturizing agents;

0.00 to 10.00% by weight/volume of an antioxidant;

0.001 to 0.10% by weight/volume of an antimicrobial preservative;

0.00 to 5.00% by weight/volume of an aromatic alcohol;

a sufficient amount of a pharmaceutically acceptable buffer to maintain the pH of the composition within the range of about 4.0 to 8.0 and QS water.

The present invention further provides a method of treating nasal conditions by administering to a nasal passage of a patient an aqueous nasal spray composition of the present invention.

DETAILED DESCRIPTION OF THE INVENTION

The aqueous nasal spray compositions of the present invention comprise a medicament in an aqueous carrier containing a water soluble polymer selected from the group consisting of polyvinylpyrrolidone and mixtures thereof.

Compositions of the present invention contain a therapeutically effective amount of at least one pharmaceutically acceptable medicament. The medicament drug may be selected from a wide range of therapeutic agents and mixtures of therapeutic agents. Illustrative categories and specific examples include. analgesics, such as ibuprofen and ketoprofen; antiasmatics, such as theophylline; antitussives, such as noscapine and chlophedinol hydrochloride; antihistamines, such as chlorpheniramine maleate, loratadine, azatadine; antinauseant, such as dimenhydrinate; decongestants, such as oxymetazoline hydrochloride; various alkaloids, such as codeine sulfate and morphine; stimulants, such as nicotine; mucolytics, such as acetylcysteine and bromhexine.

The preferred medicaments, alone or in combination, include chlorpheniramine maleate and oxymetazoline hydrochloride.

The amount of oxymetazoline hydrochloride found sufficient to effect nasal decongestion is from about 0.001 to about 0.2% by wt/vol of the total composition. Ranges of 0.01 to 0.1% of the total composition are particularly suitable. Typically, 0.05% by wt/vol is preferred for adults and children above five years of age.

The amount of chlorpheniramine maleate found sufficient for intranasal antihistamine action is from about 0.001 to about 2.0% by wt/vol of the total composition. Ranges of 0.1 to 0.5% by wt/vol is most preferable.

Various gums and polymers have been evaluated to determine the suitability of such materials as bioadhesives to extend the nasal muco-cilia clearance time of nasal spray formulations. Desired properties of a bioadhesive include solubility, clarity and compatibility in a conventional nasal spray formulation. In addition, the nasal spray composition containing the bioadhesive material was evaluated to determine the concentration effect on spray pattern and resultant mist properties.

It has been found that polyvinylpyrrolidone, a linear polymer of 1-vinyl-2-pyrrolidone, hereinafter designated PVP, extends muco-cilia clearance times of nasal spray compositions. Polyvinylpyrrolidone, also known as Povidone, is commercially available as a series of products having mean molecular weights ranging from about 10,000 to about 700,000. The various products are marketed according to average molecular weights designated K-values; e.g. GAF Corporation supplies PVP having the following K-values:

| K-value | Average Molecular Weight |
|---|---|
| 15 | about 10,000 |
| 30 | about 40,000 |
| 60 | about 160,000 |
| 90 | about 360,000 |

The nasal spray compositions of this invention contain various grades of polyvinylpyrrolidone, i.e. K-15, K-30, K-60 and K-90. The polyvinylpyrrolidone ingredient may be present as one specific grade or as a combination of two or more grades.

The most preferable polymers of polyvinylpyrrolidone for the compositions of this invention are PVP K-30 and PVP K-90.

The amount of polyvinylpyrrolidone present in the compositions of this invention is from about 0.50 to 15.00% by weight/volume of the total composition. Ranges of 0.50 to 2.5% by weight/volume of the total composition are particularly suitable and a range of 1.00 to 1.50% by weight/volume of the total composition being most preferable.

To evaluate the effect of polyvinylpyrrolidone on nasal muco-cilia clearance time, a modified procedure was employed as disclosed by E. Puchelle, et al., in Acta Otolarynogol, 91, 297–303. (1981). The procedure utilized a concentrated sodium saccharin solution as the indicator. A 100 mcl dose of water-soluble polymer test solution was sprayed into the nose. After spraying, a cotton swab saturated with saccharin solution was inserted into the nostril and wiped around the ostuim depositing the saccharin onto the nasal mucosal lining. The clearance time was defined as the time for deposit of saccharin in the ostuim to the time the saccharin was tasted in the back of the throat/mough.

Experimental results of this testing indicated that polyvinylpyrrolidone would extend nasal muco-cilia clearance times. For example, it was found that incorporation of PVP K-90 at 0.25% would extend nasal muco-cilia clearance times from the normal 8 to 10 minutes to 20 to 25 minutes.

The use of water soluble polyethylene glycol (PEG) polymers in the compositions of this invention promotes moisturization of the nasal spray compositions in the nasal cavity. Polyethylene glycol is a linear polymer formed by the addition reaction of ethylene glycol with ethylene oxide and are commercially available in average molecular weights ranging from about 200 to greater than 20,000. The commercially available grades of polyethylene glycol are marketed based on the average molecular weight, i.e. the grade nomenclature is identified with the molecular weight. For example, PEG 400 represents material with an average molecular weight of 400 and the material with an average molecular of 600 is known as PEG 600. PEG 200, 300, 400, and 600 are clear viscous liquids at room temperature; PEG 900, 1000, 1450, 3350, 4500 and 8000 are white, waxy solids.

The preferred polyethylene glycols for the compositions of this invention are PEG 400 to PEG 3350; the most preferred polyethylene glycol is PEG 1450.

The amount of polyethylene glycol present in the compositions of this invention is from about 0.00 to 15.0% by weight/volume of the total composition. Ranges of 0.5% to 10% by weight/volume of the total composition are particularly suitable and a range of 2.5 to 5% by weight/volume is most preferable.

The compositions of the present invention may contain an aromatic alcohol selected from the group consisting of benzyl alcohol and phenyl ethyl alcohol. The amount of aromatic alcohol present in the composition is from about 0 to 5.00% by weight/volume of the total composition. Ranges of 0.20–3.00% by weight/volume of the total composition are particularly suitable, and a range of 0.25 to 1.00% by weight/volume of the total composition being most preferable.

The compositions of the present invention may contain moisturizing agent. Examples of moisturizing agents useful in the compositions of this invention include propylene glycol, glycerin and the like. Mixtures of such moisturizing agents are also useful in the compositions. The amount of moisturizing agent present in the composition is from about 0 to 10% by weight/volume of the total composition. Ranges of 1.00 to 4.00% by weight/volume of the total composition are particularly suitable, and a range of 1.5 to 3.50% by weight/volume of the total composition being most preferable.

The compositions of the present invention may contain a pharmaceutically acceptable antioxidant, e.g. disodium EDTA. The amount of antioxident present in the composition is from about 0 to 0.10% by weight/volume of the total composition. Ranges of 0.01 to 0.05% by weight/volume of the total composition are particularly suitable, and a range of 0.015 to 0.030% by weight/volume of the total composition being most preferable.

The compositions of the present invention contains at least one antimicrobial preservative in the range of 0.001% to about 0.3% by weight/volume of the composition. A typical suitable preservative which functions as an antimicrobial agent includes the commercially available preservative, benzalkonium chloride in the range of about 0.02 to about 0.025% by weight/volume.

The compositions of the present invention also include pharmaceutically acceptable buffers sufficient to adjust and maintain the pH of the compositions of the present invention in the range of about 4.0 to about 8.0, preferably about 5.5 to about 7.0 and 6.25 to 6.75 being most preferable. Typically suitable buffers include citrate, phosphate and glycine.

The nasal spray compositions of the present invention is manufactured in a conventional manner by thoroughly mixing the ingredients at ambient or elevated temperatures in order to achieve solubility of ingredients where appropriate.

All percentages are by weight/volume. The definitions of components whose chemical composition is not immediately clear from the name used may be found in the CTFA Cosmetic Ingredients Dictionary, 4th Edition, 1991, published by Cosmetic Toiletry and Fragrance Association, Inc., Washington, D.C.

The following examples describe in detail the invention. It will be apparent to those skilled in the art that modifications may be practiced without departing from the purpose and intent of this disclosure.

EXAMPLE 1

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |
| PVP K-90 | 0.2500 |
| PVP K-30 | 1.0000 |
| PEG 1450 | 2.5000 |
| Benzyl Alcohol | 0.2500 |
| Benzalkonium Chloride (17% solution) | 0.0200 |
| Chlorpheniramine Maleate | 0.5000 |
| Oxymetazoline Hydrochloride | 0.0500 |

The solution is prepared according to the following procedure.

To any appropriate reaction container, add 70% of the water and heat to 50° C. Add the following: sodium phosphate monobasic, sodium phosphate dibasic, disodium EDTA and benzyl alcohol to the water. Mix each ingredient addition for at least 5 minutes. With continued mixing add the water soluble polymers, i.e. the polyvinylpyrrolidone (PVP) and the polyethylene glycol (PEG). Mix each ingredient addition for at least 5 minutes. With continued mixing add the oxymetazoline hydrochloride and chlorpheniramine maleate; mix each ingredient addition for at least 5 minutes. While mixing, add the benzalkonium chloride 17% solution and mix for at least 5 minutes. With continued mixing, the solution is cooled to 30° C. Adjust the final batch volume with water, mix until uniform and then filter using conventional filtration equipment.

EXAMPLE 2

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |
| PVP K-90 | 0.2500 |
| PVP K-30 | 1.0000 |
| PEG 1450 | 2.5000 |
| Benzyl Alcohol | 0.2500 |
| Benzalkonium Chloride (17% solution) | 0.0200 |
| Oxymetazoline Hydrochloride | 0.0500 |

The composition is prepared according to the procedure in Example 1.

EXAMPLE 3

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |
| PVP K-30 | 3.0000 |
| PEG 600 | 5.0000 |
| Benzyl Alcohol | 0.2500 |
| Benzalkonium Chloride (17% solution) | 0.0200 |
| Oxymetazoline Hydrochloride | 0.0500 |
| Chlorpheniramine Maleate | 0.5000 |

The composition is prepared according to the procedure in Example 1.

EXAMPLE 4

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |
| PVP K-30 | 3.0000 |
| PEG 1450 | 5.0000 |
| Benzyl Alcohol | 0.2500 |
| Benzalkonium Chloride (17% solution) | 0.0200 |
| Oxymetazoline Hydrochloride | 0.0500 |
| Chlorpheniramine Maleate | 0.5000 |

The composition is prepared according to the procedure in Example 1.

EXAMPLE 5

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |
| PVP K-90 | 1.0000 |
| PVP K-30 | 3.0000 |
| PEG 1450 | 2.5000 |
| Propyl glycol | 0.2500 |
| Benzalkonium Chloride (17% solution) | 0.1471 |
| Oxymetazoline Hydrochloride | 0.0500 |

The composition is prepared according to the procedure in Example 1.

EXAMPLE 6

An aqueous nasal spray composition is prepared from the following:

| INGREDIENTS | % Wt/Vol |
| --- | --- |
| Water | QS |
| Disodium EDTA | 0.0200 |
| Sodium Phosphate Dibasic | 0.0975 |
| Sodium Phosphate Monobasic | 0.5525 |

-continued

| INGREDIENTS | % Wt/Vol |
|---|---|
| PVP K-90 | 0.1000 |
| PVP K-30 | 3.0000 |
| PEG 1450 | 5.0000 |
| Propylene Glycol | 2.0000 |
| Glycerin | 0.1000 |
| Benzalkonium Chloride (17% solution) | 0.1471 |
| Oxymetazoline Hydrochloride | 0.0500 |

The composition is prepared according to the procedure in Example 1.

We claim:

1. An aqueous nasal spray composition consisting essentially of:

0.001–2% by weight/volume of a medicament selected from the group consisting of chlorpheniramine maleate, oxymetazoline hydrochloride and mixtures thereof;

0.50 to 15.00% by weight/volume of a water soluble polymer selected from the group consisting of polyvinylpyrrolidone having an average molecular weight of about 10,000 to 360,000 and mixtures thereof;

2.5 to 10.00% by weight/volume of polyethylene glycol;

1.00 to 10.00% by weight/volume of a moisturizing agent other than polyethylene glycol;

0.01 to 0.05% byweight/volume of disodium edetate;

0.001 to 0.3% by weight/volume of an antimicrobial preservative;

0.20 to 5.00% by weight/volume of an aromatic alcohol;

a sufficient amount of a pharmaceutically acceptable buffer to maintain the pH of the composition within the range of about 4.0 to 8.0; and QS water.

2. An aqueous nasal spray composition consisting essentially of:

0.001–2% by weight/volume of a medicament selected from the group consisting of chlorpheniramine maleate, oxymetazoline hydrochloride and mixtures thereof;

1.00 to 1.50% by weight/volume of a water soluble polymer selected from the group consisting of polyvinylpyrrolidone having an average molecular weight of about 10,000–360,000 and mixtures thereof;

2.5 to 5.0% by weight/volume of polyethylene glycol;

1.50 to 3.50% by weight/volume of a moisturizing agent or mixtures of moisturizing agents other than polyethylene glycol;

0.015 to 0.030% by weight/volume of disodium edetate;

0.02 to 0.025% by weight/volume of an antimicrobial preservative;

0.25 to 1.00% by weight/volume of an aromatic alcohol;

a sufficient amount of a pharmaceutically acceptable buffer to maintain the pH of the composition within the range of about 4.0 to 8.0; and QS water.

3. An aqueous nasal spray composition consisting essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-90 | 0.1000 |
| Polyvinylpyrrolidone, grade [PVP] K-30 | 3.0000 |
| Polyethylene Glycol having an average molecular weight of [PEG] 1450 | 5.0000 |
| Propylene Glycol | 2.0000 |
| Glycerin | 0.1000 |
| Benzalkonium Chloride (17% solution) | 0.1471 |
| Oxymetazoline Hydrochloride | 0.0500. |

4. The aqueous nasal spray composition of claim 1 wherein the moisturizing agent is propylene glycol; the antimicrobial preservative is benzalkonium chloride; the aromatic alcohol is benzyl alcohol; and the buffer is a phosphate buffer.

5. The aqueous nasal spray composition of claim 4 wherein the medicament is oxymetazoline hydrochloride.

6. The aqueous nasal spray composition of claim 4 wherein the medicament is chlorpheniramine maleate.

7. The aqueous nasal spray composition of claim 1 which consists essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-90 | 0.2500 |
| Polyvinylpyrrolidone, grade [PVP] K-30 | 1.0000 |
| Polyethylene Glycol having an average molecular weight of [PEG] 1450 | 2.5000 |
| Benzyl Alcohol | 0.2500 |
| Benzalkonium Chloride (17% solution) | 0.0200 |
| Chlorpheniramine Maleate | 0.5000 |
| Oxymetazoline Hydrochloride | 0.0500. |

8. The aqueous nasal spray composition of claim 1 which consists essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-90 | 0.2500 |
| Polyvinylpyrrolidone, grade [PVP] K-30 | 1.0000 |
| Polyethylene Glycol having an average molecular weight of [PEG] 1450 | 2.5000 |
| Benzyl Alcohol | 0.2500 |
| Benzalkonium Chloride (17% solution) | 0.0200 |
| Oxymetazoline Hydrochloride | 0.0500. |

9. The aqueous nasal spray composition of claim 1 which consists essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-30 | 3.0000 |
| Polyethylene Glycol having an average | 5.0000 |

| INGREDIENTS | % Wt/Vol |
|---|---|
| molecular weight of [PEG] 600 | |
| Benzyl Alcohol | 0.2500 |
| Benzalkonium Chloride (17% solution) | 0.0200 |
| Oxymetazoline Hydrochloride | 0.0500 |
| Chlorpheniramine Maleate | 0.5000. |

10. The aqueous nasal spray composition of claim 1 which consists essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-30 | 3.0000 |
| Polyethylene Glycol having an average molecular weight of [PEG] 1450 | 5.0000 |
| Benzyl Alcohol | 0.2500 |
| Benzalkonium Chloride (17% solution) | 0.0200 |
| Oxymetazoline Hydrochloride | 0.0500 |
| Chlorpheniramine Maleate | 0.5000. |

11. The aqueous nasal spray composition of claim 1 which consists essentially of:

| INGREDIENTS | % Wt/Vol |
|---|---|
| Water | QS |
| Disodium [EDTA] Edetate | 0.0200 |
| Sodium Phosphate Dibasic | 0.0975 |
| Sodium Phosphate Monobasic | 0.5525 |
| Polyvinylpyrrolidone, grade [PVP] K-90 | 0.1000 |
| Polyvinylpyrrolidone, grade [PVP] K-30 | 3.0000 |
| Polyethylene Glycol having an average molecular weight of [PEG] 1450 | 2.5000 |
| Propylene glycol | 0.2500 |
| Benzalkonium Chloride (17% solution) | 0.1471. |

* * * * *